United States Patent
Kondo et al.

(10) Patent No.: US 9,994,580 B2
(45) Date of Patent: Jun. 12, 2018

(54) PHTHALOCYANINE COMPOUND AND METHOD OF PREPARING THE SAME, COLOR FILTER CONTAINING PHTHALOCYANINE COMPOUND, AND COLORING COMPOSITION

(71) Applicant: DIC Corporation, Tokyo (JP)

(72) Inventors: Hitoshi Kondo, Chiba (JP); Yusuke Ozaki, Chiba (JP); Katsunori Shimada, Chiba (JP)

(73) Assignee: DIC CORPORATION, Tokyo (JP)

( * ) Notice: Subject to any disclaimer, the term of this patent is extended or adjusted under 35 U.S.C. 154(b) by 0 days. days.

(21) Appl. No.: 15/520,048

(22) PCT Filed: Jul. 7, 2016

(86) PCT No.: PCT/JP2016/070106
§ 371 (c)(1),
(2) Date: Apr. 18, 2017

(87) PCT Pub. No.: WO2017/029903
PCT Pub. Date: Feb. 23, 2017

(65) Prior Publication Data
US 2017/0327510 A1    Nov. 16, 2017

(30) Foreign Application Priority Data

Aug. 17, 2015   (JP) ................. 2015-160479

(51) Int. Cl.
| | | |
|---|---|---|
| *C09B 47/06* | (2006.01) | |
| *C09B 47/067* | (2006.01) | |
| *C07D 487/04* | (2006.01) | |
| *C07D 491/048* | (2006.01) | |
| *C07D 235/26* | (2006.01) | |
| *G02B 5/20* | (2006.01) | |
| *C08K 5/3447* | (2006.01) | |
| *C07D 487/22* | (2006.01) | |
| *G02B 1/04* | (2006.01) | |

(52) U.S. Cl.
CPC ......... *C07D 487/22* (2013.01); *C07D 235/26* (2013.01); *C09B 47/06* (2013.01); *G02B 1/04* (2013.01); *G02B 5/20* (2013.01)

(58) Field of Classification Search
CPC ..... C09B 47/06; C09B 47/067; C07D 487/04; C07D 491/048; C07D 235/26; G02B 5/20; C08K 5/3447
See application file for complete search history.

(56) References Cited

U.S. PATENT DOCUMENTS

| | | | |
|---|---|---|---|
| 8,809,427 B2 * | 8/2014 | Kondou | ............... C07D 235/26 524/88 |
| 2009/0018328 A1 | 1/2009 | Nagata | |
| 2012/0232194 A1 | 9/2012 | Kondou | |

FOREIGN PATENT DOCUMENTS

| | | |
|---|---|---|
| JP | 2001-064534 A | 3/2001 |
| JP | 2001-194242 A | 7/2001 |
| JP | 2006-291088 A | 10/2006 |
| JP | 2007-016203 A | 1/2007 |
| JP | 2007-039561 A | 2/2007 |
| WO | 2011/018994 A1 | 2/2011 |

OTHER PUBLICATIONS

International Written Opinion and Search Report dated Sep. 13, 2016 issued in International Patent Application No. PCT/JP2016/070106 (Partial English translation).

\* cited by examiner

*Primary Examiner* — Brenda L Coleman
(74) *Attorney, Agent, or Firm* — McDermott Will & Emery LLP

(57) ABSTRACT

Provided is a phthalocyanine compound which has a green hue without having a halogen atom, and exhibits high luminance and an excellent coloring force at the time of being used for preparing a green pixel unit of a color filter. The phthalocyanine compound of the present invention has green hues without having a halogen atom, and exhibits high luminance and an excellent coloring force at the time of being used for preparing the green pixel unit of the color filter. In addition, the phthalocyanine compound can be used not only for the color filter, but also as a colorant for a wide range of applications as a general colorant such as printing ink, paint, colored plastic, toner, and ink for ink jet.

7 Claims, No Drawings

PHTHALOCYANINE COMPOUND AND METHOD OF PREPARING THE SAME, COLOR FILTER CONTAINING PHTHALOCYANINE COMPOUND, AND COLORING COMPOSITION

CROSS REFERENCE

This patent application is the U.S. National Phase under 35 U.S.C. § 371 of International Application No. PCT/JP2016/070106, filed on Jul. 7, 2016, which claims the benefit of Japanese Patent Application No. 2015-160479, filed on Aug. 17, 2015, the entire contents of each are hereby incorporated by reference.

TECHNICAL FIELD

The present invention relates to a phthalocyanine compound which can be used as a green pigment and a method of preparing the phthalocyanine compound, and a color filter and a coloring composition containing the phthalocyanine compound.

As a representative of conventionally well-known green pigments, polyhalogenated copper phthalocyanine can be exemplified. While the polyhalogenated copper phthalocyanine has excellent fastness, it contains a large amount of halogen atoms such as chlorine and bromine in a molecule, and therefore, the safety thereof and environmental burdens have been concerned in recent years. In addition, a large amount of the halogen atoms contained in the polyhalogenated phthalocyanine causes problems in that the molecular weight becomes larger to thereby deteriorate a coloring force. For such reasons, a pigment which is a compound containing no halogen atom and can be used for green-coloring has been required.

As a method of coloring a material in green with a compound not containing a halogen atom (hereinafter, referred to as "halogen free"), a method of mixing copper phthalocyanine, which is a blue pigment, with a yellow organic pigment so as to tone into a green color has been proposed (for example, refer to PTLs 1 and 2). However, in such a method, there are problems in that two pigments having totally different chemical structures are mixed with each other, thereby causing color separation, or the light resistance is different depending on types of mixing pigments, whereby hue is greatly varied due to sunlight exposure or the like.

On the other hand, as a halogen free compound containing a single green hue, for example, a phthalocyanine compound to which an imidazolone ring is introduced is disclosed in PTL 3, and a phthalocyanine compound to which a pyrido skeleton is introduced is disclosed in PTL 4. Since the phthalocyanine compound disclosed in PTL 3 contains a green hue, there is no need to perform color toning, and the phthalocyanine compound has tolerance to an organic solvent and an acid. However, the phthalocyanine compound has a problem of low saturation.

In addition, in order to solve the above-described problems, PTL 5 discloses a phthalocyanine compound to which a disubstituted imidazolone structure in which alkyl groups are present at the N and NT symmetrically or a piperazine dione structure is introduced. However, it was difficult to disperse the phthalocyanine compound in a liquid (liquid medium) and a paste (solid), and thus the properties required for higher saturation could not be attained.

CITATION LIST

Patent Literature

PTL 1: JP-A-2001-64534
PTL 2: JP-A-2002-194242
PTL 3: JP-A-2007-16203
PTL 4: JP-A-2006-291088
PTL 5: WO2011/018994

SUMMARY OF INVENTION

Technical Problem

An object of the present invention is to provide a phthalocyanine compound which has a green hue without having a halogen atom, and has high luminance and an excellent coloring force at the time of being used for preparing a green pixel unit of a color filter.

Solution to Problem

The present inventors have conducted intensive studies in order to solve the above-described problems, and have found that one or more phthalocyanine compounds selected from the compounds represented by the following General Formula (1) and General Formula (2) have green hues without having a halogen atom, and have high luminance and an excellent coloring force at the time of being used for preparing a green pixel unit of a color filter.

Namely, the present invention provides the following.

A phthalocyanine compound represented by one or more phthalocyanine compounds selected from the compounds represented by General Formula (1) and General Formula (2).

[Chem. 1]

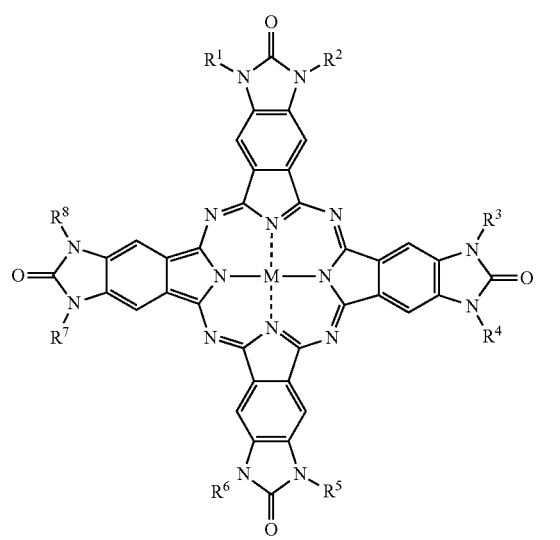

(1)

[Chem. 2]

(2)

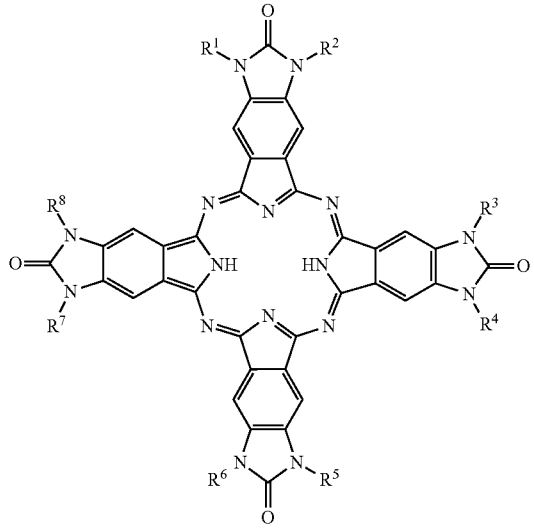

In General Formula (1) and General Formula (2), $R^1$ to $R^8$ each independently represent an alkyl group having 1 to 6 carbon atoms or an aralkyl group having 7 to 9 carbon atoms, provided that $R^1$ and $R^2$ are different from each other, $R^3$ and $R^4$ are different from each other, $R^5$ and $R^6$ are different from each other, and $R^7$ and $R^8$ are different from each other. In addition, in General Formula (1), M represents a divalent to tetravalent metal atom which may be oxidized.

A phthalocyanine compound in which the divalent to tetravalent metal atom represented by M in General Formula (1) is copper or zinc.

A phthalocyanine compound in which $R^1$ to $R^8$ in General Formula (1) or General Formula (2) each independently represent an alkyl group having 1 to 4 carbon atoms, provided that $R^1$ and $R^2$ are different from each other, $R^3$ and $R^4$ are different from each other, $R^5$ and $R^6$ are different from each other, and $R^7$ and $R^8$ are different from each other.

A compound which is a synthetic raw material of the phthalocyanine compound, and is one or more selected from the compounds represented by General Formula (3) and General Formula (4).

[Chem. 3]

(3)

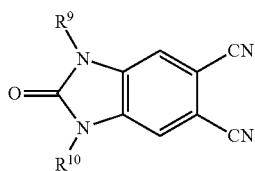

In General Formula (3), $R^9$ and $R^{10}$ each independently represent an alkyl group having 1 to 6 carbon atoms or an aralkyl group having 7 to 9 carbon atoms, provided that $R^9$ and $R^{10}$ are different from each other.

[Chem. 4]

(4)

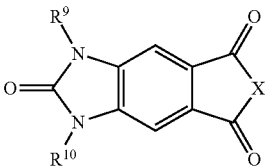

In General Formula (4), $R^9$ and $R^{10}$ each independently represent an alkyl group having 1 to 6 carbon atoms or an aralkyl group having 7 to 9 carbon atoms, provided that $R^9$ and $R^{10}$ are different from each other, and X represents —O— or —NH—.

A method of preparing a phthalocyanine compound includes causing only one or more compounds selected from the compounds represented by General Formula (3) and General Formula (4) or a mixture thereof with a metal salt corresponding to the divalent to tetravalent metal atom represented by M in General Formula (1) to perform heat condensation.

A color filter containing the above phthalocyanine compound.

A coloring composition containing the above phthalocyanine compound.

Advantageous Effects of Invention

According to the present invention, there is provided a phthalocyanine compound which has a green hue, and has high luminance and an excellent coloring force at the time of being used for preparing a green pixel unit of a color filter.

In addition, the phthalocyanine compound of the present invention has features of halogen free, high safety, and low environmental impact. Accordingly, for applications in which environmental measures are required, it is very useful as a replacement for a halogenated phthalocyanine pigment which is an existing green pigment.

The phthalocyanine compound of the present invention has the aforementioned features, and thus can be used not only for the color filter, but also as a colorant for a wide range of applications as a general colorant such as printing ink, paint, colored plastic, toner, and ink for ink jet.

DESCRIPTION OF EMBODIMENTS

The phthalocyanine compound represented by General Formula (1) or General Formula (2) of the present invention is a compound in which a N,N'-disubstituted imidazolone structure having two substituents in the imidazolone structure, which are selected from an alkyl group and an aralkyl group and are different from each other, is introduced to each of four benzene skeletons of phthalocyanine. Note that, in the present application, a compound in which metal is complexed in a center portion of phthalocyanine is represented by General Formula (1), and a non-metal compound is represented by General Formula (2). Both compounds have a green color.

Note that, the phthalocyanine compound represented by General Formula (1) is referred to as compound (1), and the phthalocyanine compound represented by General Formula (2) is referred to as compound (2).

Synthesis examples of the compound (1) or the compound (2) of the present invention are described as follows. In order to synthesize the compound (1) or the compound (2), first, a dicyano benzimidazolone compound represented by the following General Formula (3), which is a dinitrile compound having a N,N'-disubstituted imidazolone ring which is an intermediate thereof, or a phthalic anhydride and a phthalimide compound which are represented by the following General Formula (4) are synthesized by the following synthesis method.

[Chem. 5]

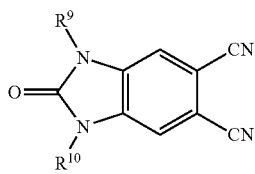

(3)

In General Formula (3), $R^9$ and $R^{10}$ each independently represent an alkyl group having 1 to 6 carbon atoms or an aralkyl group having 7 to 9 carbon atoms, provided that $R^9$ and $R^{10}$ are different from each other.

[Chem. 6]

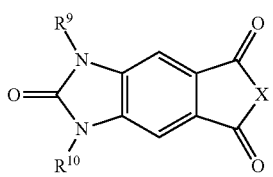

(4)

In General Formula (4), $R^9$ and $R^{10}$ each independently represent an alkyl group having 1 to 6 carbon atoms or an aralkyl group having 7 to 9 carbon atoms provided that $R^9$ and $R^{10}$ are different from each other. X represents O or NH.

N,N'-disubstituted dicyano benzimidazolone compound and Synthesis of derivatives In General Formula (3), the synthesis can be performed according to the following method. A compound (6) is obtained by substituting a nitro group of a compound (5), which is obtained by dinitration of 4-position and 5-position of o-dibromobenzene, with an amine. Then, the bromine atoms are substituted with cyano groups, and the nitro group is reduced to an amino group. An obtained diamino compound (8) is reacted with phosgene, chlorocarbonate ester, urea, or 1,1'-carbonylbis-1H-imidazole in an organic solvent such as acetonitrile at 0° C. to 130° C. for 1 to 6 hours so as to obtain a dicyanobenzimidazolone compound (hereinafter, referred to as "compound (9)") represented by the following Formula (9). Subsequently, the compound (9) is reacted with one of compounds such as an alkyl halide and an aralkyl halide in an organic solvent such as N,N-dimethyl formamide, N-methyl-2-pyrrolidinone, and dimethyl sulfoxide under the existence of a base such as sodium hydride, cesium carbonate, potassium carbonate, and potassium t-butoxide so as to obtain a N,N'-disubstituted dicyano benzimidazolon compound (hereinafter, referred to as a "compound (3)") represented by General Formula (3). The details of the synthesis method are described in Chemical Communications, 2236 (2002).

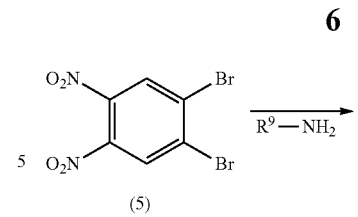

(5)

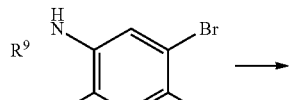

(6)

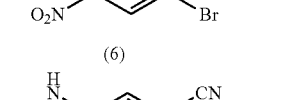

(7)

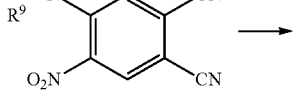

(8)

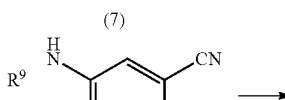

(9)

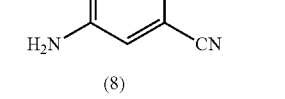

(3)

In the reaction formula, Y represents a chlorine atom, a bromine atom, an iodine atom, or a sulfonate ester group such as a tosyl group, a mesyl group, and a trifluoromethanesulfonyl group.

In addition, a compound (7) can be synthesized by substituting a bromine atom of 4-bromo-5-nitrophthalonitrile (10) with an amine. The details of this method are described in Mendeleev Communications, 78 (2000).

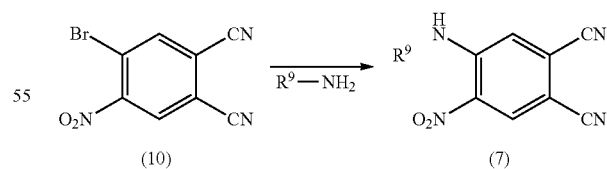

In General Formula (4), the synthesis can be performed according to the following method. A dicarboxylic acid compound (11) can be obtained by hydrolyzing the compound (3). When the compound (11) is dehydrated by reacting with an acetic anhydride or the like, it is possible to obtain an acid anhydride represented by X=O in General Formula (4). Then, when the compound represented by X=O compound in General Formula (4) reacts with ammonia or formamide, it is possible to a compound represented by X=NH in General Formula (4).

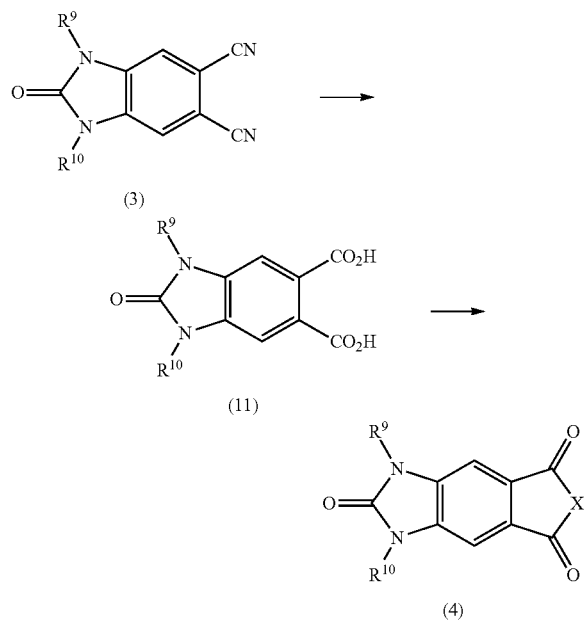

Synthesis of Compound (1) or Compound (2)

The compound (1) of the present invention can be obtained by subjecting heat condensation to the compound (3) or the compound (4) obtained by the above synthesis method, and metal salt corresponding to the divalent to tetravalent metal atoms which are represented by M in General Formula (1) in an organic solvent at a temperature in a range of 120° C. to 250° C.

In addition, the compound (2) of the present invention can be obtained according to the aforementioned synthesis method without using the metal salt corresponding to the divalent to tetravalent metal atoms.

Examples of the divalent to tetravalent metal atoms which are represented by M in General Formula (1) include magnesium, aluminum, titanium, vanadium, iron, cobalt, nickel, copper, zinc, platinum, and palladium. Among them, titanium, vanadium, iron, cobalt, nickel, copper, and zinc are preferable, and vanadium, cobalt, copper, and zinc are most preferably. Further, these metals may be oxidized.

As the metal salt corresponding to the divalent to tetravalent metal atoms, various types of metal salts such as a halogen salt, an acetate salt, a sulfate salt, a nitrate salt, and a carbonate salt can be used, and among them, the halogen salt and the acetate salt are preferable.

Examples of the organic solvent used at the time of synthesizing the compound (1) or the compound (2) include alcohols, glycols, trichlorobenzene, quinoline, α-chloronaphthalene, nitrobenzene, sulfolane, and N,N-dimethyl formamide. In addition, the reaction may be performed without a solvent.

In addition, at the time of synthesizing the compound (1) or the compound (2), an alkali or an organic amine such as 1,8-diazabicyclo[5,4,0]undec-7-ene (hereinafter, referred to as "DBU"), 1,5-diazabicyclo [4,3,0]non-5-ene (hereinafter, referred to as "DBN"), and cyclohexyl amine is preferably used as a catalyst from the aspect of the improvement of the yield.

Examples of the alkyl group having 1 to 6 carbon atoms which is represented by $R^1$ to $R^8$ in the above compound (1) and compound (2) include a methyl group, an ethyl group, a propyl group, an isopropyl group, a butyl group, a pentyl group, a hexyl group. Examples of the aralkyl group having 7 to 9 carbon atoms include a benzyl group, 2-phenylethyl group, and 3-phenylpropyl group. When the number of carbon atoms of the alkyl group or the aralkyl group is increased, the durability against the organic solvent tends to be deteriorated.

Among them, as $R^1$ to $R^8$ in General Formula (1) and General Formula (2), a methyl group, an ethyl group, a propyl group and a butyl group are preferable, and a methyl group, an ethyl group, and a propyl group are particularly preferable.

The compound disclosed in PTL 3, in which $R^1$ to $R^8$ in General Formula (1) and General Formula (2) contain a hydrogen atom has low saturation, and the aforementioned compound causes strong aggregation. The reason for this is considered that the compound contains a hydrogen atom on the nitrogen atom of the imidazolone ring, and thus a strong hydrogen bonding force between the molecules is generated, and the aggregation becomes severe, thereby deteriorating the saturation. In the compound (1) or the compound (2) of the present application, the substituent other hydrogen is present on the nitrogen atom of the imidazolone ring, and thus it is considered that a high saturation hue can be obtained without the aggregation. Further, in the present invention, $R^1$ and $R^2$, $R^3$ and $R^4$, $R^5$ and $R^6$, and $R^7$ and $R^8$ are different groups from each other. When the substituents are asymmetricized, it is considered that as compared with a case where $R^1$ to $R^8$ are the same groups as each other, aggregation of pigment particles is suppressed while dispersibility is improved, and thus viscosity of a dispersion liquid is greatly reduced.

With the above synthesis method, the compound (1) or the compound (2) can be obtained as a green crude pigment, and when it is used as a colorant, it is preferable to perform a pigmenting treatment. Examples of a method of the pigmenting treatment include a grinding treatment such as solvent salt milling, salt milling, dry milling, solvent milling, and acid pasting, and a solvent heating treatment. With such pigmenting treatments, it is possible to adjust the particle size of the pigment at the same time.

In a case where the phthalocyanine compound of the present invention is used as a green pigment, it is preferable that the phthalocyanine compound is subjected to the above pigmenting treatment so as to adjust the particle size of the pigment to be in a range of 0.01 to 1.5 μm. In an electron micrograph of the obtained pigment, the solvent salt milling in which a pigment having the average length/width ratio of the particles (a so-called average aspect ratio) which is less than 3 and is close to 1, and having the narrower particle diameter distribution can be obtained is preferably used as a pigmenting treatment.

In addition, in a case where the phthalocyanine compound is used as a green pigment as described above, it may be simply mixed or may be pulverized and mixed with an organic pigment or an inorganic pigment which can be selected from the various kinds thereof. Further, as in the acid pasting, it may be in a form of a mixture or a solid solution having a primary particle size. In addition, it is possible to use a pigment derivative, a surfactant, and an additive in combination for dispersibility, suppression of particle growth control, heat resistance, weather resistance, and light fastness.

In various conventionally known applications, even though the phthalocyanine compound of the present invention undergoes thermal history at a high temperature, it has small hue variation with excellent heat resistance. From this aspect, in a case of being used to manufacture a color filter pixel unit, it is possible to obtain a color filter for a liquid crystal display device which is capable of realizing excellent image display with small hue variation.

In order to prepare a photosensitive composition for a color filter pixel unit, for example, the organic pigment composition of the present invention, a photosensitive resin, a photopolymerization initiator, and an organic solvent for solving the above resin are mixed with each other as essential components. As a method of preparing the photosensitive composition, a method of preparing a dispersion liquid by using the organic pigment composition of the present invention and the organic solvent, and a dispersant as necessary, and then adding a photosensitive resin to the dispersion liquid is generally used.

In the color filter of the present invention, as a backlight source, it is possible to use any one of a cold-cathode tube (CCFL light source) in the related art, a white light emitting diode (LED) light source, three independent LED light sources, and a white organic electro luminescence (EL) light source.

In addition, it is possible to add an organic pigment derivative, a dispersant, and a water-insoluble synthetic resin being liquid at room temperature to the phthalocyanine compound of the present invention. Examples of the organic pigment derivative includes a sulfonic acid derivative of non-metal or metal phthalocyanine, a N-(dialkylamino) methyl derivative of non-metal or metal phthalocyanine, a N-(dialkylaminoalkyl) sulfonic acid amide derivative of non-metal or metal phthalocyanine, a quinophthalone sulfonic acid derivative, and a phthalocyanine sulfonic acid. Examples of the dispersant include DISPERBYK 130, DISPERBYK 161, DISPERBYK 162, DISPERBYK 163, DISPERBYK 170, DISPERBYK 171, DISPERBYK 174, DISPERBYK 180, DISPERBYK 182, DISPERBYK 183, DISPERBYK 184, DISPERBYK 185, DISPERBYK 2000, DISPERBYK 2001, DISPERBYK 2020, DISPERBYK 2050, DISPERBYK 2070, DISPERBYK 2096, DISPERBYK 2150, DISPERBYK LPN21116, and DISPERBYK LPN 6919 which are prepared by BYK Japan KK., EFKA 46, EFKA 47, EFKA 452, EFKA LP4008, EFKA 4009, EFKA LP4010, EFKA LP4050, EFKA LP4055, EFKA 400, EFKA 401, EFKA 402, EFKA 403, EFKA 450, EFKA 451, EFKA 453, EFKA 4540, EFKA 4550, EFKA LP4560, EFKA 120, EFKA 150, EFKA 1501, EFKA 1502, and EFKA 1503 which are prepared by BASF, SOLSPERSE 3000, SOLSPERSE 9000, SOLSPERSE 13240, SOLSPERSE 13650, SOLSPERSE 13940, SOLSPERSE 17000, SOLSPERSE 18000, SOLSPERSE 20000, SOLSPERSE 21000, SOLSPERSE 24000, SOLSPERSE 26000, SOLSPERSE 27000, SOLSPERSE 28000, SOLSPERSE 32000, SOLSPERSE 36000, SOLSPERSE 37000, SOLSPERSE 38000, SOLSPERSE 41000, SOLSPERSE 42000, SOLSPERSE 43000, SOLSPERSE 46000, SOLSPERSE 54000, and SOLSPERSE 71000 which are prepared by Lubrizol Corporation, AJISPER PB711, AJISPER PB821, AJISPER PB822, AJISPER PB814, AJISPER PN411, and AJISPER PA111 which are prepared by Ajinomoto Co., Inc. Examples of the water-insoluble synthetic resin being liquid at room temperature include an acrylic resin; a urethane resin; an alkyd resin; natural rosin such as wood rosin, gum rosin, and tall oil rosin; modified rosin such as polymerized rosin, disproportionated rosin, hydrogenated rosin, oxidized rosin, and maleated rosin; and a rosin derivative such as rosin amine, lime rosin, a rosin alkylene oxide adduct, a rosin alkyd adduct, and a rosin modified phenol. The addition of the derivative, the dispersant, or the resin contributes to the improvement of the reduction in flocculation, the improvement of the dispersion stability, and the improvement of the viscosity properties of dispersion.

The phthalocyanine compound of the present invention has a hue suitable for preparing the color filter green pixel unit, and as necessary, halogenated copper phthalocyanine (C.I. Pigment Green 7 and 36) and halogenated zinc phthalocyanine (C.I. Pigment Green 58) are used in combination in a range of 0.1 to 50 parts with respect to 100 parts by mass. In addition, it is possible to adjust the hue and the transmission wavelength by adding various yellow pigments such as C.I. Pigment Yellow 129, C.I. Pigment Yellow 138, and C.I. Pigment Yellow 139 for the purpose of the color toning.

The phthalocyanine compound of the present invention has the light fastness suitable for preparing the color filter green pixel unit, and as necessary, it is possible to use an antioxidant which has the nonvolatile content in a range of 0.1 to 10 parts, and preferably in a range of 0.5 to 8 parts with respect to 100 parts of phthalocyanine compound. Here, the antioxidant is a generic name for additives to prevent oxidative deterioration, and includes a material (an antioxidant in narrow sense) preventing the oxidative degradation due to heat, and a material (called as a light stabilizer in narrow sense) preventing the oxidative deterioration due to light (mainly ultraviolet light).

Such an antioxidant includes a material having an action of capturing radicals and preventing auto oxidation (a radical chain prevention action), and a material having an action of decomposing hydroperoxide (peroxide) into a harmless material (a peroxidede decomposition action). The former is referred to as a primary antioxidant, and the latter is referred to as a secondary antioxidant. An antioxidant which has both actions of the primary and secondary antioxidants is also known. Examples of the primary antioxidant include various antioxidants such as phenol-based (including hindered phenol-based) antioxidant and amine-based (including hindered amine-based) antioxidant, and typical examples of the secondary antioxidant include antioxidants such as a sulfur-based antioxidant and a phosphorus-based antioxidant.

When the phthalocyanine compound of the present invention is used in combination with a cationic resin as necessary, it is possible to further improve the heat resistance and the light fastness.

As such a cationic resin, an acrylic resin, a polyurethane resin, an epoxy resin, and a polyamide resin are preferably used from the aspect that hue variation is small and the heat resistance of the color filter can be greatly improved under the thermal history.

In the present invention, the ratio of the phthalocyanine compound to the nonvolatile content of the cationic resin is not particularly limited; however, the nonvolatile content of the cationic resin is in a range of equal to or greater than 0.1 parts and less than 10 parts, is preferably in a range of 0.5 to 5, and particularly 1 to 3 parts, with respect to 100 parts of the phthalocyanine compound.

When preparing the coloring composition which contains the phthalocyanine compound and the cationic resin, the heating of the compound and the resin can be performed in a closed system, in the range of 30 minutes to 5 hours under stirring at a temperature at which no problem occurs in the compound itself, after mixing both of the phthalocyanine compound and the cationic resin. When a pressurized state is formed in this manner, as described above, the cationic resin permeates into the voids of the compound particles, and thus a further excellent effect can be realized as compared with a case of simply coating the particle surface.

A photolithography method is a representative manufacturing method of the color filter in which the phthalocyanine compound of the present invention is used, and this method is performed in such a manner that a photocurable composition to be described below is coated on a surface on the side on which a black matrix of a transparent substrate for a color filter is provided, a coated surface is heated and dried (pre-baked), is irradiated with ultraviolet via a photomask so as to perform pattern exposure, a portion of the photocurable compound which corresponds to the pixel unit is cured, unexposed portions are developed by using a developer, and non-pixel units are removed so as to fix the pixel unit on the transparent substrate. In this method, a pixel unit formed of a cured pigmented film of the photocurable composition is formed on the transparent substrate.

A photocurable composition to be described below is prepared for each color of red, green, and blue, and the above operation is repeated so as to manufacture a color filter having colored pixel units of red, green, and blue at predetermined positions. The green pixel unit can be formed of the phthalocyanine compound of the present invention. Note that, conventionally well-known red pigment and blue pigment can be used to prepare the photocurable composition for forming the red pixel unit and the blue pixel unit.

Examples of the pigment for forming the red pixel unit include C.I. Pigment Red 177, 209, 242, and 254, and examples of the pigment for forming the blue pixel unit include C.I. Pigment Blue 1, 15:6, 60, and 80. A yellow pigment also can be used in combination so as to form the red pixel unit. In addition, a violet pigment can be used so as to form the blue pixel unit. After that, as necessary, the entire color filter can be subjected to a heat treatment (post bake) such that an unreacted photocurable compound is thermally cured.

Examples of a method of coating the photocurable composition to be described below on a transparent substrate such as glass include a spin coating method, a roll coating method, and an ink jet method.

A drying condition for a coated film obtained by coating the photocurable composition on the transparent substrate is differentiated depending on the types of and mixing ratio of the respective components; however, in general, the drying is performed at a temperature of 50° C. to 150° C. for 1 to 15 minutes. In addition, as the light used for photocuring the photocurable composition, a light beam having a wavelength range of 200 to 500 nm is preferably used. It is possible to use various light sources that emit light in this wavelength range.

Examples of a developing method include a liquid deposition method, a dipping method, and a spray method. After exposing and developing the photocurable composition, a transparent substrate on which required color pixel units are formed is washed by water and dried. The color filter obtained in this way is subjected to the heat treatment (post bake) at a temperature of 90° C. to 280° C. for a predetermined time by heating device such as a hot plate and an oven so as to remove a volatile component in the colored coating film, and unreacted photocurable compound remaining in the cured pigmented film of the photocurable composition is thermally cured, and thereby a color filter is completed.

The photocurable composition for forming the green pixel unit of the color filter can be prepared by mixing the phthalocyanine compound of the present invention, the dispersant, the photocurable compound, and the organic solvent as essential components, and as necessary, a thermoplastic resin. In a case where a colored resin film for forming the green pixel unit requires toughness that can withstand baking or the like which is performed in the actual manufacturing of the color filter, at the time of preparing the photocurable composition, it is necessary to use not only the photocurable compound, but also a thermoplastic resin. In a case where the thermoplastic resin is used in combination, an organic solvent which solves the thermoplastic resin is preferably used.

As a method of preparing a photocurable composition, there is a typical method performed in such a manner that the phthalocyanine compound of the present invention, the organic solvent, and the dispersant are used as essential components, these are stirred and dispersed so as to be uniformly mixed with each other, a dispersion liquid for forming a pixel unit of a color filter is prepared first, and then the photocurable compound, and the thermoplastic resin and the photopolymerization initiator, as necessary, are added to the dispersion liquid so as to form the above photocurable composition.

Examples of the organic solvent include an aromatic solvent such as toluene, xylene, and methoxybenzene, an acetic acid ester solvent such as ethyl acetate, butyl acetate, propylene glycol monomethyl ether acetate, and propylene glycol monoethyl ether acetate, a propionate-based solvent such as ethoxyethyl propionate, an alcohol-based solvents such as methanol and ethanol, an ether solvent such as butyl cellosolve, propylene glycol monomethyl ether, diethylene glycol ethyl ether, and diethylene glycol dimethyl ether, a ketone solvent such as methyl ethyl ketone, methyl isobutyl ketone, and cyclohexanone, an aliphatic hydrocarbon solvent such as hexane, a nitrogen compound solvents such as N,N-dimethyl formamide, γ-butyrolactam, N-methyl-2-pyrrolidone, and aniline, a lactone solvent such as γ-butyrolactone, carbamic acid esters such as a mixture of methyl carbamate and ethyl carbamate (48:52), and water. Particularly suitable examples of the organic solvent include a polar solvent being water-soluble such as a propionate-based solvent, an alcohol-based solvent, an ether-based solvent, a ketone-based solvent, a nitrogen compound-based solvent, a lactone-based solvent, and water.

Examples of the thermoplastic resin used for preparing the photocurable composition include a urethane resin, an acrylic resin, a polyamide resin, a polyimide resin, a styrene maleic acid resin, and a styrene maleic anhydride resin.

Examples of the photocurable compound include a bifunctional monomer 1,6-hexanediol diacrylate, ethylene glycol diacrylate, neopentyl glycol diacrylate, triethylene glycol diacrylate, bis (acryloxyethoxy) bisphenol A, and 3-methyl pentanediol diacrylate, a polyfunctional monomer having a relatively small molecular weight such as trimethylolpropanetriacrylate, pentaerythritoltriacrylate, tris [2-(meth)acryloyloxyethyl) isocyanurate, dipentaerythritol hexaacrylate, and dipentaerythritol pentaacrylate, a polyfunctional monomer having a relatively large molecular weight such as polyester acrylate, polyurethane acrylate, and polyether acrylate.

Examples of a photopolymerization initiator include acetophenone, benzophenone, benzyl dimethyl ketal, benzoyl peroxide, 2-chlorothioxanthone, 1,3-bis(4'-azidobenzal)-2-propane, 1,3-bis(4'-azidobenzal)-2-propane-2'-sulfonic acid, and 4,4'-diazidostilbene-2,2'-disulfonic acid. Examples of commercially available photopolymerization initiator include "IRGACURE (product name)-184" prepared by Chiba Specialty Chemicals Company, "IRGA- CURE (product name)-369", "DAROCURE (product name)-1173", "LUCIRIN TPO" prepared by BASF, "KAYACURE (product name) DETX" and "KAYACURE (product name) OA" prepared by Nippon Kayaku Co., Ltd., "VICURE 10" and "VICURE 55" prepared by Stauffer Chemical Company, "TRIGONAL PI" prepared by Akzo Corporation, "SANDRAY 1000" prepared by Sandoz Inc, "DEEP" prepared by Upjohn Inc, and "BIIMIDAZOLE" prepared by Kurogane Kasei Co., Ltd.

In addition, a known and commonly used photosensitizer may be used in combination with the photopolymerization initiator. Examples of the photosensitizer include amines, ureas, compounds containing a sulfur atom, compounds containing a phosphorus atom, compounds containing a chlorine atom, nitriles or other compounds containing nitrogen atom. These can be used alone, or two or more types thereof can be used in combination.

The ratio of the photopolymerization initiator is not particularly limited, but is preferably in a range of 0.1 to 30% by mass with respect to a compound containing a photopolymerizable or photocurable functional group. If the ratio is less than 0.1%, the sensitivity during photocuring tends to be decreased, on the other hand, if the ratio is more than 30%, a crystal of the photopolymerization initiator is precipitated when a coated film of a resist is dried and thus the physical properties of the coated film may be degraded.

Using the materials as described above, 300 to 1,000 parts by mass of the organic solvent and 1 to 100 parts by mass of the dispersant with respect to 100 parts by mass of the phthalocyanine compound of the present invention are stirred and dispersed so as to be uniformly mixed with each other. Thus, the pigment dispersion liquid can be prepared. Subsequently, 3 to 20 parts by mass of the thermoplastic resin and the photocurable compound in total with respect to 1 part by mass of the phthalocyanine compound of the present invention, 0.05 to 3 parts by mass of the photopolymerization initiator with respect to 1 part by mass of the photocurable compound, and optionally an organic solvent are added to the pigment dispersion liquid and stirred and dispersed so as to be uniformly mixed with each other. Thus, a photocurable composition for forming a pixel unit of a color filter can be prepared.

The conventionally known organic solvent or aqueous alkali solution can be used as the developer. In particular, in the case where the photocurable composition contains a thermoplastic resin or a photocurable compound, and at least one of the thermoplastic resin and the photocurable compound has an acid value and exhibits alkali solubility, washing with an aqueous alkali solution is effective for the formation of pixel portions of a color filter.

Among the dispersion method of the phthalocyanine compound of the present invention, a method for manufacturing a pixel unit of a color filter by photolithography has been described in detail; however, regarding the pixel unit of the color filter manufactured by using the phthalocyanine compound of the present invention, a green pixel unit may be formed by another method such as an electrodeposition method, a transfer method, a micelle electrolysis method, a photovoltaic electrodeposition (PVED) method, an inkjet method, a reverse printing method, or a heat curing method to produce a color filter.

The color filter can be manufactured by the following method. The photo-curable compositions for three colors are prepared using, as organic pigments, a red pigment, a blue pigment, and the phthalocyanine compound of the present invention. A liquid crystal material is sealed between a pair of transparent electrodes disposed in parallel with each other, and the transparent electrodes are divided into discontinuous minute sections. Using the photocurable compositions, red, green, and blue pixel units of the color filter are alternately formed in a pattern in the corresponding minute sections divided into a lattice shape by the black matrix on the transparent electrode. Alternatively, the pixel units of the color filter are formed on a substrate and then the transparent electrodes are provided thereon.

Further, the phthalocyanine compound of the present invention can provide a coloring pigment dispersion having excellent clearness and luminance and can be applied to paint, plastics (resin molded articles), printing inks, rubbers, leather, textiles, toner for developing an electrostatic image, ink for ink jet recording, and thermal transfer ink, in addition to color filter applications.

The coloring composition of the present invention is a composition containing the phthalocyanine compound of the present invention as a colorant, and a synthetic resin, and examples thereof include printing ink, paint, colored plastic, toner, ink for an ink jet, a color paste for a color filter, and a color resist. Here, an application (medium) of the phthalocyanine compound of the present invention is not particularly limited as long as coloring is possible.

Examples of the synthetic resin used for prepared the coloring composition of the present invention include a polymerization resin and a condensation resin, and particularly include a urea resin/formaldehyde resin and a melamine/formaldehyde resin, an alkyd resin, a phenol resin, a polyester resin, a polyamide resin, polyvinyl chloride, polyurethane, acrylic/melamine, polystyrene, cellulose ether, nitrocellulose, polyacrylate, polyacrylonitrile, and polyolefin. These can be used alone or a mixture thereof can be used.

The coloring composition of the present invention can be easily prepared by mixing, for example, 100 to 2,000 parts of synthetic resin (nonvolatile content) with respect to 100 parts of the phthalocyanine compound of the present invention, depending on the purpose of the coloring.

In the present invention, the average particle size of primary particles is measured as follows. First, particles in a field of view are micrographed using a transmission electron microscope or a scanning electron microscope. The largest inner diameters (maximum lengths) of 50 primary particles constituting aggregates on a two-dimensional image are determined. The average of the maximum lengths of the 50 particles is defined as the average particle size of primary particles.

EXAMPLES

Hereinafter, the present invention will be described in more detail with reference to examples. For the analysis of synthesized compounds, the following devices were used unless otherwise noted.

NMR analysis: "JNM-LA300", nuclear magnetic resonance apparatus manufactured by JEOL Ltd., TMS is used as an internal standard substance Infrared spectroscopic analysis: "FT/IR-4200", infrared spectrophotometer manufactured by JASCO Corporation.

FD/MS analysis: "JMS-700", mass spectrometer manufactured by JEOL Ltd.

UV-visible spectroscopy analysis: "U-4100", spectrophotometer manufactured by Hitachi, Ltd.

Synthesis Example 1

(Synthesis of Dicyano Benzimidazolone Compound Intermediate in which $R^9$ is an Ethyl Group, and $R^{10}$ is Hydrogen in General Formula (3))

Under a nitrogen atmosphere, 26.0 g of 4-amino-5-ethylaminophthalonitrile and 28.0 g of 1,1'-carbonyldiimidazole were weighed and put in a flask, 260 ml of acetonitrile (dehydrated) was added and the mixture was heated under reflux. After stirring for six hours, the heating was stopped so as to cool the reaction solution down to room temperature. The generated precipitate was filtered, and washed by acetonitrile, and then was dried by blowing air at 90° C. for one night so as to obtain 23.7 g of a compound represented by Formula (12) (yield of 80%)

Regarding the obtained compound, $^1$H- and $^{13}$C-NMR analysis in a dimethyl sulfoxide (hereinafter, referred to as "DMSO")-d6 solution, the infrared spectroscopic analysis by a KBr pellete method, and the FD/MS analysis were performed and the following analysis results were obtained.

<NMR Analysis>

$^1$H—NMR (DMSO-d6) δ ppm: 1.19 (t, j=7.2 Hz, 3 H), 3.87 (q, j=7.2 Hz, 2 H), 7.65 (s, 1 H), 8.00 (s, 1 H)

$^{13}$C—NMR (DMSO-d6) δ ppm: 13.3, 35.5, 106.7, 106.8, 112.5, 113.2, 116.8, 116.9, 131.9, 133.3, 153.9

<Infrared Spectroscopic Analysis>

3250 (N—H stretching vibration), 3056 (an ethyl group C—H stretching vibration), 2239 (a cyano group CN stretching vibration), 1737 (carbonyl group CO stretching vibration) cm$^{-1}$ <FD/MS Analysis>

212M$^+$

From the above results, the compound obtained in Synthesis example 1 was confirmed to be a dicyano benzimidazolone compound represented by the following formula.

[Chem. 7]

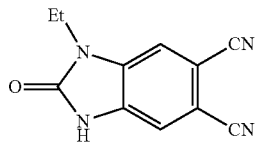

(12)

Synthesis Example 2

(Synthesis of Dicyano Benzimidazolone Compound in which R$^9$ is an ethyl group, and R$^{10}$ is a methyl group in General Formula (3))

Under a nitrogen atmosphere, 2.07 g of 60% sodium hydride was weighted and put in a flask and 120 ml of N,N-dimethyl formamide (dehydration) was added and the mixture was stirred. 10.0 g of compound represented by Formula (12) was added to the mixture while maintaining a temperature in a range of 20° C. to 25° C., and then stirred for 30 minutes. Then, 7.36 g of methyl iodide which was dissolved in 10 mL of N,N-dimethyl formamide (dehydration) was added to the mixture and the mixture was stirred at a temperature in a range of 25° C. to 30° C. for three hours. A reaction mixture was poured in the mixture solution of 230 g of ice water and 100 g of saturated ammonium chloride aqueous solution. The generated precipitate was filtered, washed by water and n-hexane, and dried by blowing air at 90° C. for one night. Thus 10.5 g of compound represented by Formula (13) was obtained. (Yield of 98%)

Regarding the obtained compound in Synthesis example 2, $^1$H— and $^{13}$C—NMR analysis in the DMSO-d6 solution, the infrared spectroscopic analysis by a KBr pellete method, and the FD/MS analysis were performed and the following analysis results were obtained.

<NMR Analysis>

$^1$H—NMR (DMSO-d6) δ ppm: 1.20 (t, j=7.1 Hz and 3 H), 3.38 (s, 3 H), 3.92 (q, j=7.1 Hz, 2 H), 7.99 (s, 1 H), 8.06 (s, 1 H)

$^{13}$C—NMR (DMSO-d6) δ ppm: 13.3, 27.6, 36.1, 106.7, 106.8, 112.5, 112.7, 116.8, 132.0, 133.1, 153.4

<Infrared Spectroscopic Analysis>

3070, 2930 (C—H stretching vibration of an ethyl group and a methyl group), 2230 (a cyano group CN stretching vibration), and 1718 (carbonyl group CO stretching vibration) cm$^{-1}$ <FD/MS Analysis>

226 M$^+$

From the above results, the compound obtained in Synthesis example 2 was confirmed to be a compound represented by the Formula (13).

[Chem. 8]

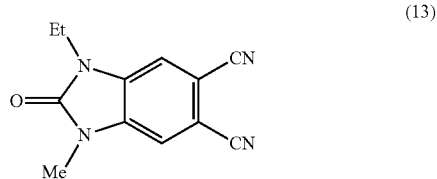

(13)

Synthesis Example 3

(Synthesis of Phthalocyanine Compound (14))

Under a nitrogen atmosphere, 11.0 g of compound (13) obtained in Synthesis example 2, 2.33 g of zinc acetate, and 7.40 g of 1,8-diazabicyclo [5,4,0] undec-7-ene (DBU) were added into 110 ml of 1-pentanol, and the mixture was stirred and heated under reflux for eight hours. After cooling the reaction solution down to equal to or lower than 70° C., the generated precipitate was separated by filtration. The obtained crude product was sequentially washed by thermal methanol, 1 mol/l of hydrochloric acid water, 7% by mass of ammonia water, thermal N,N-dimethyl formamide, and methanol, and thereby 8.84 g of desired phthalocyanine compound (14) was obtained as a green solid. (Yield of 75%)

Regarding the obtained compound in Synthesis example 3, FD/MS analysis and the infrared spectroscopic analysis by a KBr pellete method were performed and the following analysis results were obtained.

<FD/MS Analysis>

968 M$^+$

<Infrared Spectroscopic Analysis>

1695 (carbonyl group CO stretching vibration), 1490, 1415, 1080 cm$^{-1}$

From the above analysis results, the compound obtained in Synthesis example 3 was confirmed to be a regioisomer mixture of the phthalocyanine compound represented by the following Formula (14).

[Chem. 9]

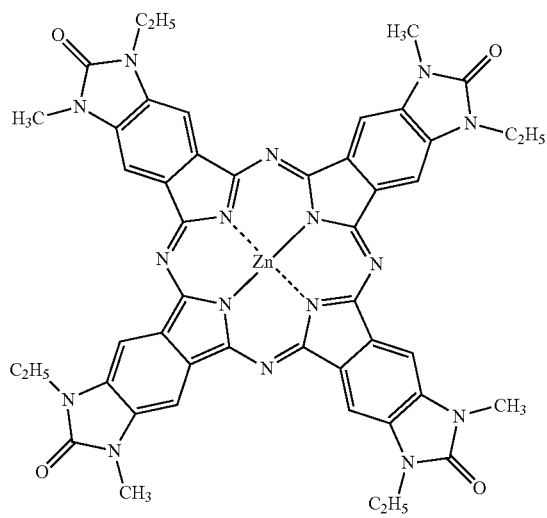

(14)

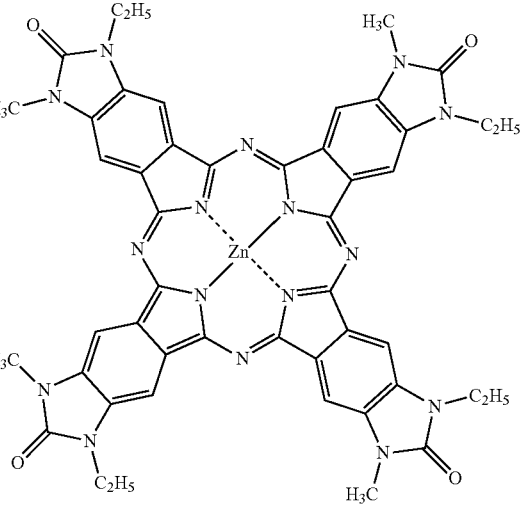

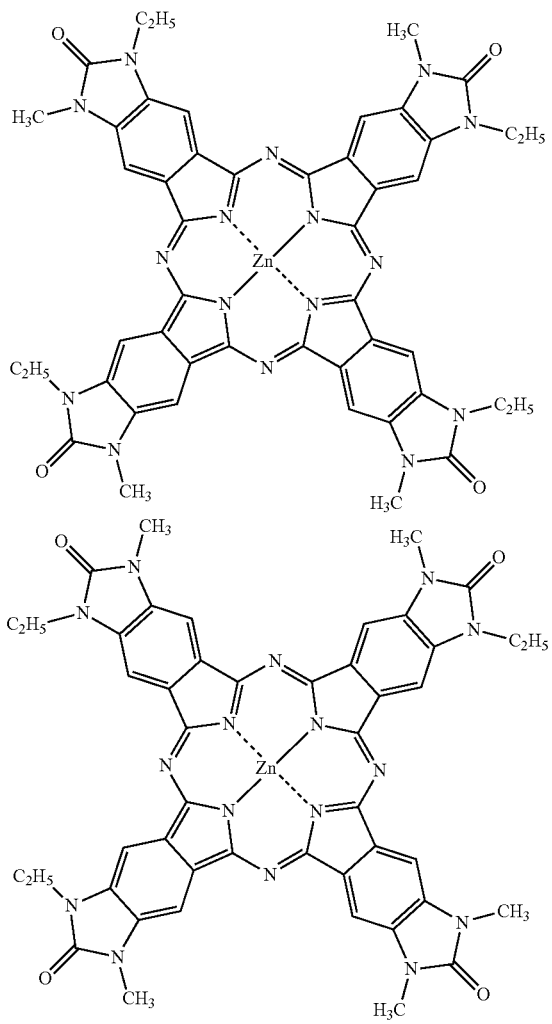

Synthesis Example 4

(Synthesis of Phthalocyanine Compound (15))

Under a nitrogen atmosphere, 9.90 g of compound (13) obtained in Synthesis example 2, 1.18 g of copper chloride (I), and 6.81 g of 1,8-diazabicyclo [5,4,0]undec-7-ene (DBU) were added into 100 ml of 1-pentanol, and the mixture was heated under reflux for eight hours with stirring. After cooling the reaction solution down to equal to or lower than 70° C., the generated precipitate was separated by filtration. The obtained crude product was sequentially washed by thermal methanol, 1 mol/l of hydrochloric acid water, 7% by mass of ammonia water, thermal N,N-dimethyl formamide, and methanol, and thereby 8.67 g of desired phthalocyanine compound (15) was obtained as a green solid. (Yield of 82%)

Regarding the obtained compound in Synthesis example 4, FD/MS analysis and the infrared spectroscopic analysis by a KBr pellete method were performed and the following analysis results were obtained.

<FD/MS Analysis>

967 M$^+$

<Infrared Spectroscopic Analysis>

1715 (carbonyl group CO stretching vibration), 1490, 1440, 1420, 1080 cm$^{-1}$

From the above analysis results, the compound obtained in Synthesis example 4 was confirmed to be a regioisomer mixture of the phthalocyanine compound represented by the following Formula (15).

[Chem. 10]

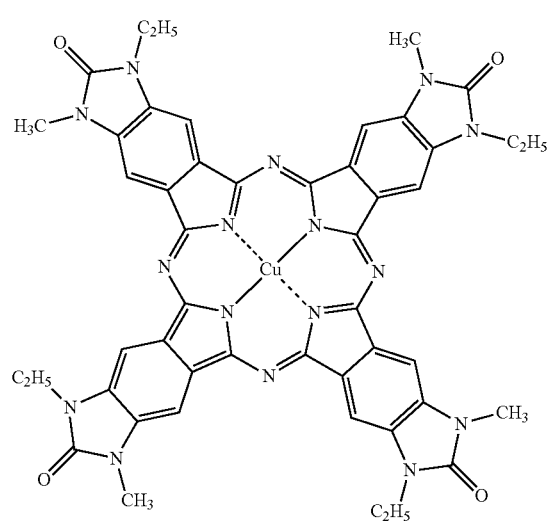

(15)

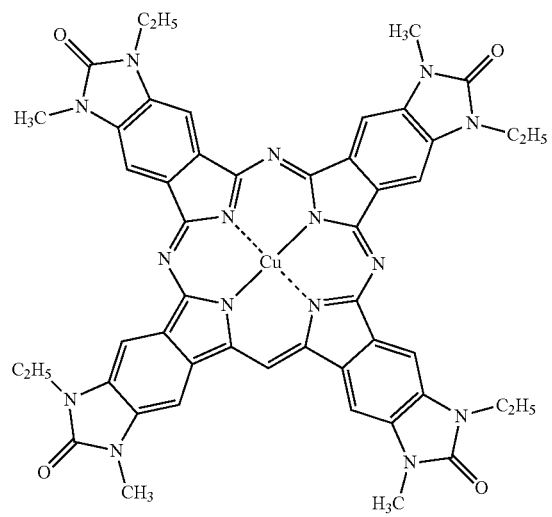

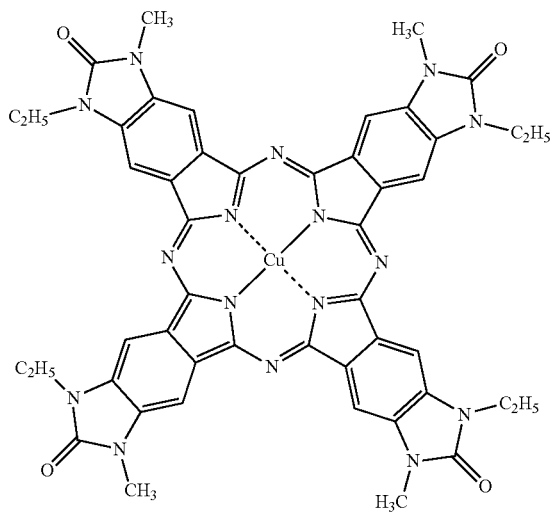

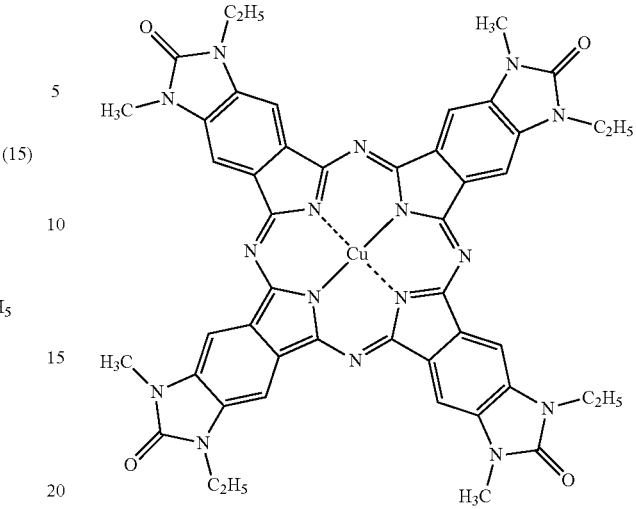

Synthesis Example 5

(Synthesis of Phthalocyanine Compound (16))

Under a nitrogen atmosphere, 10.0 g of compound (13) obtained in Synthesis example 2, and 7.40 g of 1,8-diazabicyclo[5,4,0]undec-7-ene (DBU) were added into 100 ml of 1-pentanol, and the mixture was heated under reflux for nine hours with stirring. After cooling the reaction solution down to equal to or lower than 70° C., the generated precipitate was separated by filtration. The obtained crude product was sequentially washed by thermal methanol, 1 mol/l of hydrochloric acid water, 7% by mass of ammonia water, thermal N,N-dimethyl formamide, and methanol, and thereby 6.79 g of desired phthalocyanine compound (16) was obtained as a green solid. (Yield of 68%)

Regarding the obtained compound in Synthesis example 5, FD/MS analysis and the infrared spectroscopic analysis by a KBr pellete method were performed and the following analysis results were obtained.

<FD/MS Analysis>

906 M+

<Infrared Spectroscopic Analysis>

1714 (carbonyl group CO stretching vibration), 1495, 1475, 1073, 1025 $cm^{-1}$

From the above analysis results, the compound obtained in Synthesis example 5 was confirmed to be a regioisomer mixture of the phthalocyanine compound represented by the following Formula (16).

[Chem. 11]

(16)

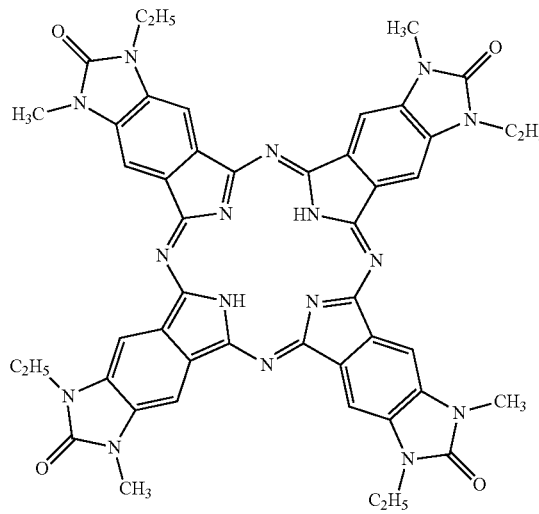

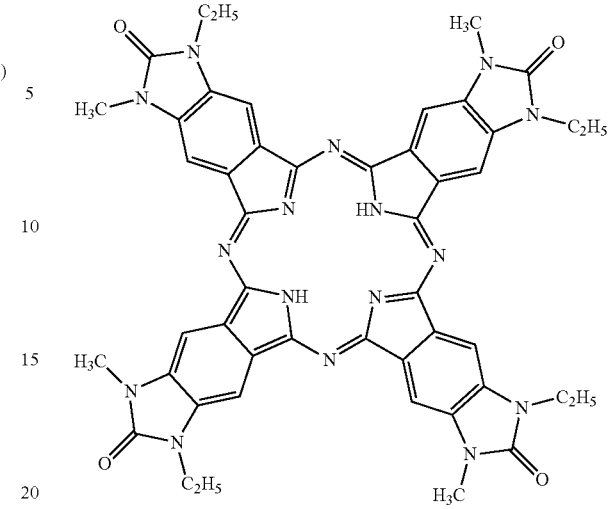

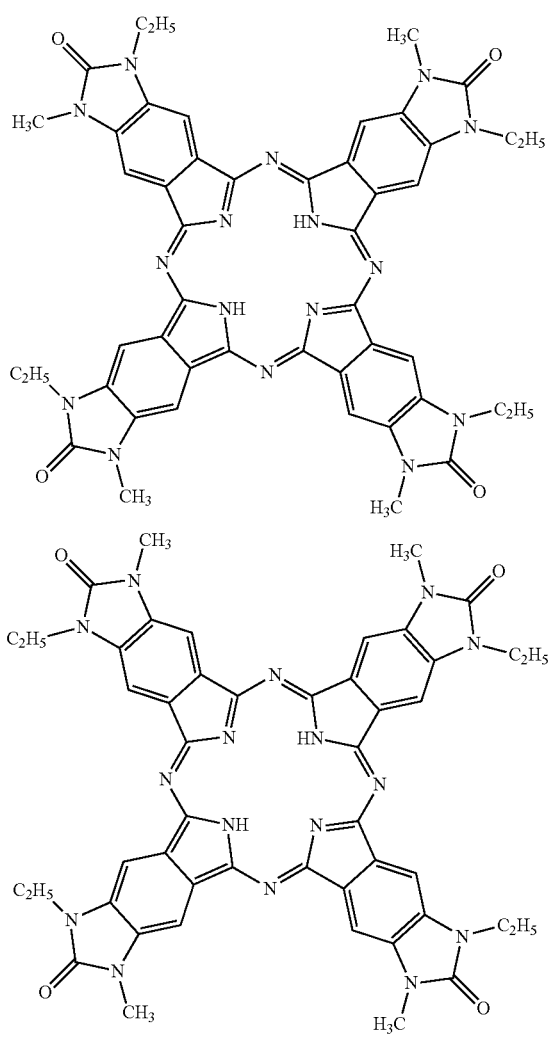

(Pigmentation Method)

0.50 parts by mass of the phthalocyanine compound obtained in Synthesis Example 3 to 5 was ground together with 1.50 parts by mass of sodium chloride and 0.75 parts by mass of diethylene glycol. Thereafter, this mixture was poured into 600 parts by mass of warm water and stirred for one hour. The water-insoluble material was separated by filtration, thoroughly washed with warm water, and dried by blowing air at 90° C. to make a pigment. The pigment particle size was equal to or less than 300 nm, the average length/width ratio of the particles was equal to or less than 3. Using the obtained green pigment of the phthalocyanine compound, the following dispersion test and color filter evaluation test were performed.

[Pigment Dispersion 1]

1.30 parts by mass of phthalocyanine compound (14) obtained in Synthesis example 3 was put into a polyethylene container, 11.5 parts by mass of propylene glycol monomethyl ether acetate, 3.62 parts by mass of DISPERBYK (product name) LPN 21116 (prepared by BYK Japan KK.), 3.62 parts by mass acrylic resin solution UNIDIC (Registered trademark) ZL-295 (prepared by DIC Corporation), and 50 parts by mass of sepule beads in a range of 0.3 to 0.4 ramp were added to the polyethylene container, and the mixture was dispersed for two hours by using a paint conditioner (manufactured by TOYO SEIKI Co., Ltd). 4.0 parts by mass of propylene glycol monomethyl ether acetate was added to the obtained dispersion and the dispersion was further dispersed for 30 minutes by using the paint conditioner, and thereby a pigment dispersion was obtained.

[Pigment Dispersion 2]

1.25 parts by mass of phthalocyanine compound (15) obtained in Synthesis example 4 and 0.05 parts by mass of SOLSPERSE 5000 (prepared by Lubrizol Japan Ltd) were put into a polyethylene container, 11.5 parts by mass of propylene glycol monomethyl ether acetate, 3.62 parts by mass of DISPERBYK (product name) LPN 21116 (prepared by BYK Japan KK.), 3.62 parts by mass acrylic resin solution UNIDIC (Registered trademark) ZL-295 (prepared by DIC Corporation), and 50 parts by mass of sepule beads in a range of 0.3 to 0.4 mmφ were added to the polyethylene container, and the mixture was dispersed for two hours by using a paint conditioner (manufactured by TOYO SEIKI Co., Ltd). 4.0 parts by mass of propylene glycol monomethyl ether acetate was added to the obtained dispersion and the dispersion was further dispersed for 30 minutes by using the paint conditioner, and thereby a pigment dispersion was obtained.

[Pigment Dispersion 3]

A pigment dispersion was obtained according to the same method as that used for the pigment dispersion 1 except that a phthalocyanine compound synthesized according to a method of Example 3 disclosed in Japanese Patent No. 4962812 was used instead of the phthalocyanine compound (14) obtained in the Synthesis example 3.

[Pigment Dispersion 4]

A pigment dispersion was obtained according to the same method as that used for the pigment dispersion 2 except that a phthalocyanine compound synthesized according to a method of Example 4 disclosed in Japanese Patent No. 4962812 was used instead of the phthalocyanine compound (15) obtained in the Synthesis example 4.

[Pigment Dispersion 5]

A pigment dispersion was obtained according to the same method as that used for the pigment dispersion 1 except that Pigment Green 58 (A110 prepared by DIC Corporation) was used instead of the phthalocyanine compound (14), obtained in the Synthesis example 3.

(Viscosity Measurement of Pigment Dispersion)

Regarding the obtained dispersion, the viscosity of the dispersion liquid was measured by means of a viscometer (TVE-25 model viscometer, manufactured by TOKI SANGYO CO., LTD), and a dispersed particle size was measured by means of a particle size distribution measuring device (dynamic light scattering type particle size distribution measuring apparatus LB-550, manufactured by HORIBA, Ltd.). The results thereof are indicated in Table 1.

TABLE 1

| Pigment dispersion | Viscosity (mPa · s) | Dispersed particle size (nm) | |
|---|---|---|---|
| | | D50 | D90 |
| Pigment dispersion 1 | 7.3 | 72 | 97 |
| Pigment dispersion 2 | 8.8 | 86 | 125 |
| Pigment dispersion 3 | 51 | 120 | 166 |
| Pigment dispersion 4 | Equal to or greater than 60 | — | — |
| Pigment dispersion 5 | 5.9 | 60 | 80 |

It is found that the pigment dispersions 1 and 2 have the low viscosity of the dispersion liquid and the small dispersed particle size as compared with the pigment dispersions 3 and 4. The pigment dispersion 4 has high viscosity and thus it was not possible to measure the dispersed particle size.

Example 1

A glass substrate was coated with the pigment dispersion 1 with a spin coater. A rotational speed of the spin coater was set to be 600, 800, 1000, and 1200 rpm, and four types of glass plates with different coating film thicknesses of the composition was created. The glass plates obtained in this way, which was coated with the composition, was heated at 90° C. for 3 minutes, and thereby a color filter green pixel unit was obtained.

Example 2

A green pixel unit was obtained according to the same method as that used in Example 1 except that the pigment dispersion 2 was used instead of the pigment dispersion 1.

Comparative Example 1

A green pixel unit was obtained according to the same method as that used in Example 1 except that the pigment dispersion 3 was used instead of the pigment dispersion 1.

Comparative Example 2

The pigment dispersion 4 has high viscosity, and thus it was not possible to uniformly coat the glass substrate by using the spin coater.

Example of color filter evaluation test

Regarding the color filter created in Examples and Comparative Examples, values of chromaticity and luminance after performing the post bake (baking performed at 230° C. for one hour) and a value of color difference before and after performing the post bake were indicated in Table 2. The chromaticity and the luminance were measured by means of a spectrophotometer CM-3500d manufactured by KONICA MINOLTA, INC, and the contrast was measured by means of a contrast tester CT-1/DULBM manufactured by TSUBO-SAKA ELECTRIC CO., LTD.

TABLE 2

| Example No. | Chromaticity x (y = 0.550) | Luminance Y (y = 0.550) | Contrast (y = 0.550) | Color difference before and after performing ΔE*ab |
|---|---|---|---|---|
| Example 1 | 0.248 | 49.9 | 5820 | 2.0 |
| Comparative Example 1 | 0.250 | 49.0 | 3000 | 2.9 |
| Example 2 | 0.217 | 38.7 | 6640 | 1.5 |
| Comparative Example 2 | Not possible to create coated film | — | — | — |

Example 1 is excellent in both of the luminance and the contrast as compared with Comparative Example 1. Further, it was possible to create a coating film for evaluation in Example 2 unlike Comparative Example 2.

Comparative Example 3

A green pixel unit was obtained according to the same method as that used in Example 1 except that the pigment dispersion 5 was used instead of the pigment dispersion 1.

When the color filter green pixel unit created in Examples 1 and 2, and Comparative Example 3 satisfied Chromaticity y=0.500, the film thickness thereof was measured by means of a confocal microscope (OPTELICS C130 manufactured by Lasertec Corporation).

TABLE 3

| | Film thickness (μm) |
|---|---|
| Example 1 | 0.86 |
| Example 2 | 1.20 |
| Comparative Example 3 | 1.89 |

It is found that in Examples 1 and 2, when the same chromaticity is set, the film thickness is thin and the coloring force is strong as compared with Comparative Example 3.

The invention claimed is:

1. A phthalocyanine compound which is one or more selected from compounds represented by Formula (1) and Formula (2):

[Chem. 1]

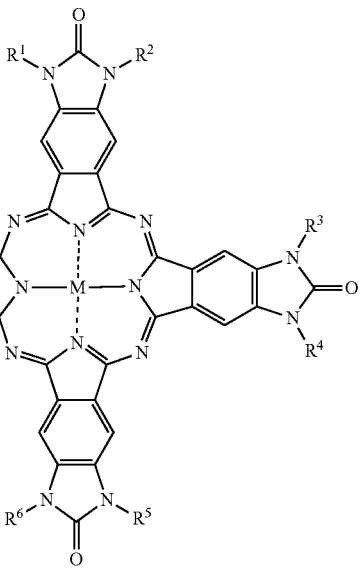

(1)

[Chem. 2]

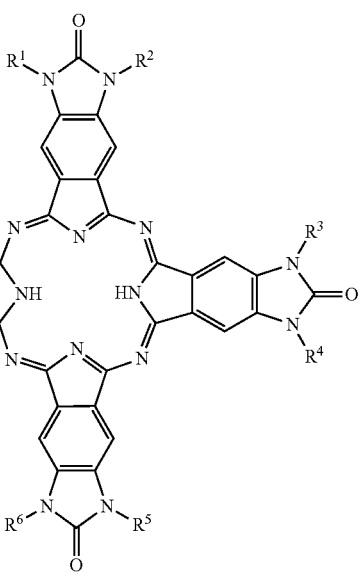

(2)

wherein, in Formulas (1) and (2), $R^1$, $R^2$, $R^3$, $R^4$, $R^5$, $R^6$, $R^7$ and $R^8$ each independently represent an alkyl group having 1 to 6 carbon atoms or an aralkyl group having 7 to 9 carbon atoms, provided that $R^1$ and $R^2$ are different from each other, $R^3$ and $R^4$ are different from each other, $R^5$ and $R^6$ are different from each other, and $R^7$ and $R^8$ are different from each other, and in Formula (1), M is a divalent to tetravalent metal atom which may be oxidized.

2. The phthalocyanine compound according to claim 1, wherein the divalent to tetravalent metal atom represented by M in Formula (1) is copper or zinc.

3. The phthalocyanine compound according to claim 1, wherein $R^1$, $R^2$, $R^3$, $R^4$, $R^5$, $R^6$, $R^7$ and $R^8$ in Formulas (1) or (2) each independently represent an alkyl group having 1 to 4 carbon atoms, provided that $R^1$ and $R^2$ are different from each other, $R^3$ and $R^4$ are different from each other, $R^5$ and $R^6$ are different from each other, and $R^7$ and $R^8$ are different from each other.

4. A compound which is a synthetic raw material of the phthalocyanine compound according to claim 1, and is one or more selected from compounds represented by Formula (3) and Formula (4):

[Chem. 3]

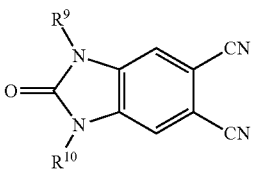

(3)

in Formula (3), $R^9$ and $R^{10}$ each independently represent an alkyl group having 1 to 6 carbon atoms or an aralkyl group having 7 to 9 carbon atoms, provided that $R^9$ and $R^{10}$ are different from each other:

[Chem. 4]

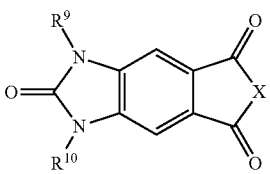

(4)

in Formula (4), $R^9$ and $R^{10}$ each independently represent an alkyl group having 1 to 6 carbon atoms or an aralkyl group having 7 to 9 carbon atoms, provided that $R^9$ and $R^{10}$ are different from each other, and X represents —O— or —NH—.

5. A method of preparing of the phthalocyanine compound according to claim 1, the method comprising:
causing only one or more compounds selected from compounds represented by Formula (3) and Formula (4) or a mixture thereof with a metal salt corresponding to the divalent to tetravalent metal atom represented by M in Formula (1) to perform heat condensation.

6. A color filter comprising:
the phthalocyanine compound according to claim 1.

7. A coloring composition comprising:
the phthalocyanine compound according to claim 1.

* * * * *